(12) United States Patent
Mandeau et al.

(10) Patent No.: US 8,734,784 B2
(45) Date of Patent: May 27, 2014

(54) **COMPOSITION COMPRISING A COMBINATION OF AN ELDER EXTRACT AND A STRAIN OF *L. PARACASEI, L. BULGARICUS* OR *S. THERMOPHILUS***

(75) Inventors: Anne Mandeau, Toulouse (FR); Christine Libon, Castanet-Tolosan (FR); Marie-Françoise Aries, Escalquens (FR); Gianfranco Grompone, Paris (FR); Violeta Niborski, Cachan (FR)

(73) Assignees: Pierre Fabre Medicament, Boulogne-Billancourt (FR); Compagnie Gervais Danone, Paris (FR)

( * ) Notice: Subject to any disclaimer, the term of this patent is extended or adjusted under 35 U.S.C. 154(b) by 316 days.

(21) Appl. No.: 13/124,402

(22) PCT Filed: Oct. 16, 2009

(86) PCT No.: PCT/EP2009/063534
§ 371 (c)(1),
(2), (4) Date: Jul. 11, 2011

(87) PCT Pub. No.: WO2010/043696
PCT Pub. Date: Apr. 22, 2010

(65) Prior Publication Data
US 2011/0262409 A1    Oct. 27, 2011

(30) Foreign Application Priority Data
Oct. 17, 2008    (FR) ..................... 08 57102

(51) Int. Cl.
*A01N 63/00* (2006.01)
*A61K 36/00* (2006.01)

(52) U.S. Cl.
USPC ............... 424/93.4; 424/93.44; 424/93.45; 424/725

(58) Field of Classification Search
None
See application file for complete search history.

(56) References Cited

U.S. PATENT DOCUMENTS

| | | | |
|---|---|---|---|
| 5,077,060 A * | 12/1991 | Prahl | 426/15 |
| 7,214,396 B2 * | 5/2007 | Rivier | 426/72 |
| 7,604,809 B2 * | 10/2009 | Postaire et al. | 424/206.1 |
| 2004/0029127 A1 | 2/2004 | Postaire et al. | |
| 2006/0233895 A1 * | 10/2006 | Brown | 424/725 |
| 2007/0098847 A1 | 5/2007 | Tessier | |
| 2010/0129334 A1 | 5/2010 | Samson-Villeger et al. | |

FOREIGN PATENT DOCUMENTS

| | | |
|---|---|---|
| DE | 202007008818 U1 | 8/2008 |
| EP | 0794707 B1 | 11/1998 |
| EP | 1283714 B1 | 7/2006 |
| FR | 2912657 A1 | 8/2008 |
| WO | WO 96/20607 A1 | 7/1996 |
| WO | WO 01/89541 A1 | 11/2001 |
| WO | WO 2005/070221 A1 | 8/2005 |
| WO | WO 2007/083123 A1 | 7/2007 |
| WO | WO 2008/043856 A1 | 4/2008 |

OTHER PUBLICATIONS

Lee et al., "Extraction of Anthocyanins and Polyphenolics from Blueberry-Processing Waste," Journal of Food Science, vol. 69, No. 7, 2004, pp. C564-C573.
Lodoen et al., "Natural Killer Cells as an Initial Defense Against Pathogens," Current Opinion in Immunology, vol. 18, 2006, pp. 391-398.
Ministry for the Economy, "Decree No. 88-1203 of Dec. 30, 1988 Relating to Fermented Milk and Yoghurt," Finance and Budget, Journal Officiel De La République Française, Dec. 31, 1988, p. 16750.
Vivier et al., "Functions of Natural Killer Cells," Nature Immunology, vol. 9, No. 5, May 2008, pp. 503-510.
Wu et al., "Characterization of Anthocyanins and Proanthocyanidins in Some Cultivars of Ribes, Aronia, and Sambucus and Their Antioxidant Capacity," Journal of Agricultural and Food Chemistry, vol. 52, 2004, pp. 7846-7856.
Zakay-Rones et al., "Randomized Study of the Efficacy and Safety of Oral Elderberry Extract in the Treatment of Influenza A and B Virus Infection," The Journal of International Medical Research, vol. 32, 2004, pp. 132-140, XP002433349.
"Codex Standard for Fermented Milks, Codex Standard 243-2003," (prepared by the Commission of Codex Alimentarius under the auspices of the FAO and the WHO, and published by the Information Division of FAO), available online: http://www.codexalimentarius.net; vol. 12, 2003, pp. 1-8.
Barak et al., "The Effect of Sambucol, a Black Elderberry-Based, Natural Product, on the Production of Human Cytokines: I. Inflammatory Cytokines," European Cytokine Network, vol. 12, No. 2, Jun. 2001, pp. 290-296.
Brønnum-Hansen et al., Anthocyanin Colorants from Elderberry (*Sambucus nigra* L.) IV. Further Studies on Production of Liquid Extracts, Concentrates and Freeze Dried Powders, Journal of Food Technology, vol. 21, 1986, pp. 605-614.
Di Santo, "Natural Killer Cell Developmental Pathways: A Question of Balance," The Annual Review of Immunology, vol. 24, 2006, pp. 257-286.
Etiévant et al., "F 11782, a Dual Inhibitor of Topoisomerases I and II with an Original Mechanism of Action in Vitro, and Markedly Superior in Vivo Antitumour Activity, Relative to Three Other Dual Topoisomerase Inhibitors, Intoplicin . . . ," Cancer Chemother Pharmacol, vol. 46, 2000, pp. 101-113.
European Pharmacopoeia 7.0, "2.5.33. Total Protein," pp. 147-150 (in particular the paragraph Method 7, pp. 149-150).

(Continued)

*Primary Examiner* — Vera Afremova
(74) *Attorney, Agent, or Firm* — Birch, Stewart, Kolasch & Birch, LLP (57) ABSTRACT

The invention relates to a composition comprising a combination of an elder extract (*Sambucus nigra*) and a strain of *L. paracasei, L. casei, L. bulgaricus* or *S. thermophilus*, intended for stimulating immunity and/or promoting an anti-infectious and/or anti-inflammatory response.

8 Claims, 4 Drawing Sheets

(56) References Cited

OTHER PUBLICATIONS

Foligne et al., "Correlation between in Vitro and in Vivo Immunomodulatory Properties of Lactic Acid Bacteria," World Journal of Gastroenterology, vol. 13, No. 2, Jan. 14, 2007, pp. 236-243.
Food and Agriculture Organization of the United Nations and World Health Organization, "Health and Nutritional Properties of Probiotics in Food Including Powder Milk with Live Lactic Acid Bacteria," Córdoba, Argentina, Oct. 1-4, 2001, pp. 1-34.
Girard et al., "Membrane Processing of Fruit Juices and Beverages: A Review," Critical Reviews in Food Science and Nutrition, vol. 40, No. 2, 2000, pp. 91-157.
International Search Report issued on Mar. 17, 2010 for International Application No. PCT/EP2009/063534.

* cited by examiner

COMPOSITION COMPRISING A COMBINATION OF AN ELDER EXTRACT AND A STRAIN OF *L. PARACASEI, L. BULGARICUS* OR *S. THERMOPHILUS*

The present invention relates to a composition comprising a combination of an elder extract and at least one strain of *L. paracasei, L. casei, L. bulgaricus* or *S. thermophilus* preferably intended for stimulating immunity and/or for promoting an anti-infectious and/or anti-inflammatory response.

Elder or *Sambucus nigra L.* is a member of the Adoxaceae family.

The genus *Sambucus* includes 25 species distributed worldwide in temperate regions. The black elder, *S. nigra* ssp. *nigra*, is widely grown in Europe (Denmark, Italy and Austria), in Northern Africa and in Western Asia. The Canadian elder, *S. nigra* ssp. *canadensis*, originates from North-East of North America and is grown in Oregon, Pennsylvania and Kansas, although its selection is performed in Canada.

The following various elder organs: corks, roots, stems, flowers, leaves and fruits are traditionally used in various fields including medicine, food industry and manufacture of tools and toys. The major industrial productions currently relate to the production of elderberry extracts directed to the nutraceutic markets and colorant industry.

Some publications report the effect of elderberry extract on the production of cytokines («The effect of Sambucol, a black elderberry-based, natural product, on the production of animal cytokines I. Inflammatory cytokines» Eur. Cytokine Netw. 2001 April-June; 12(2): 290-296). In particular the effect of an elderberry extract on reducing the symptoms related to an influenza infection due to Influenza viruses (A and/or B and/or C) has already been disclosed as well as its antiviral effect on the type 1 herpes simplex virus, the respiratory syncytial virus and the parainfluenza virus. («Randomized Study of the Efficacy and Safety of Oral Elderberry Extract in the treatment of Influenza A and B Virus Infections» The Journal of Int. Med. Res. 2004; 32:132-140).

Many scientific studies have demonstrated the advantageous effects on health of certain microorganisms contained in fermented foods, especially dairy products. These microorganisms are commonly referred to as «probiotics». According to the widely accepted current definition, probiotics are: «live microorganisms which when consumed in adequate amounts have an advantageous effect on the host's health» (see the FAO/WHO report on Evaluation of Health and Nutritional Properties of Probiotics in Food including Powder Milk with Live Lactic Acid Bacteria; Cordoba, Argentina; 1-4 Oct. 2001).

It has been shown in patent applications WO96/20607, EP0794707, EP1283714, and FR2912657, that the consumption of food products containing probiotic bacteria can result in desirable effects on health, especially through balancing the intestine flora, improving resistance to infections, and modulating the immune response.

Probiotic microorganisms used in human diet are generally lactic acid bacteria, belonging mainly to the *Lactobacillus* and *Bifidobacterium* strains, and in particular to the *Lactobacillus paracasei* species.

Patent Application US 2006/0233895 discloses a composition comprising an elder extract that can optionally be combined with a probiotic such as L-casei. However, this composition necessarily contains a mixture of Uncaria Tomentosa, Pau d'Arco, scrutellaria baicalensis and artemisin. Furthermore, this composition is not intended for stimulating immunity but is for treating the Lyme disease caused by a bacterial infection, which is accordingly highly different from influenza-type virus infections.

The inventors have investigated the in vitro effect of a combination comprising an elder extract and at least one strain of *L. paracasei, L. casei, L. bulgaricus* or *S. thermophilus* on the production of non-specific immunity mediators (cytokines) by peripheral blood mononuclear cells (PBMC). The results of this type of in vitro model are highly correlated with the effects that can be obtained in-vivo (World J. Gastroenterol. 2007; 13(2): 236-243).

The PBMC cell model is used to investigate the response ability of cells of the human immune system. This response is revealed by IL-10, IFN gamma and IL-6 cytokine production.

Upon inflammatory stress, IL-10 is produced by the macrophages to regulate pro-inflammatory cytokine production such as TNF-alpha. It promotes a reduction in antigen display, reduces T cell proliferation, but in the presence of IL-2, -4 and -7 can act as a differentiation factor of cytotoxic T cells. IL-10 improves antibody-producing B cell survival.

IFN-gamma or type II IFN has some antiviral activity and inhibits cell proliferation. However, IFN-gamma is essentially immunomodulating, contrary to type I IFNs (alpha- and beta-IFN) which have mainly an antiviral activity. IFN-gamma activates macrophages and NK cells: therefore it influences cytotoxic mechanisms. It modulates T cell proliferation and differentiation and is known to promote type 1 immune responses and, conversely to inhibit the type 2.

IL-6 is a pleiotropic cytokine influencing antigen-specific immune responses and inflammatory reactions. It is one of the major physiological mediators of acute phase reaction. IL-6 is a B-cell differentiation factor and an activation factor for T-cells. In the presence of IL-2, IL-6 induces the differentiation of mature and immature T-cells into cytotoxic T-cells. IL-6 and IL-3 synergise in vitro in promoting the proliferation of multipotent hematopoietic progenitor cells. IL-6 is also a thrombopoietin that induces the maturation of megakaryocytes in vitro and increases platelet counts in vivo.

Both components (elder extract and *L. paracasei, L. casei, L. bulgaricus* or *S. thermophilus* strain) act on human immune system cells to potentiate immune responses so that the body is better prepared for any infectious aggression or any morbid inflammatory process. The results obtained have shown that, very surprisingly and unexpectedly, these components, when in the same composition, act synergistic on non-specific immune responses.

The present invention thus relates to a composition comprising a combination of an elder extract and at least one strain of *L. paracasei, L. casei, L. bulgaricus* or *S. thermophilus*. Preferably said composition does not contain Uncaria Tomentosa and/or Pau d'Arco and/or Scrutellaria baicalensis and/or artemisin, in particular such as described in US 2006/0233895. In particular, it does not contain a mixture of Uncaria Tomentosa, Pau d'Arco, Scrutellaria baicalensis, and artemisin.

In one specific embodiment, the composition according to the invention concerns a composition comprising a combination of an elder extract and at least one strain of *L. paracasei*.

In one specific embodiment, the composition according to the invention can be prepared by the process comprising the following steps:

a) preparing a combination of an elder extract and at least one *L. paracasei, L. casei, L. bulgaricus* or *S. thermophilus* strain;

b) adding the combination to the composition according to the present invention.

In this case the combination is thus prepared before it is added to the composition. However it is also possible to prepare a composition according to the present invention by adding each of the constituents of the combination separately to the composition, i.e. without preparing the combination beforehand.

In one specific embodiment, the composition according to the invention concerns a composition comprising a combination of an elder extract and at least one strain of *L. paracasei, L. casei, L. bulgaricus* and/or *S. thermophilus*.

Preferably, the composition according to the invention is for oral administration.

Preferably the composition according to the present invention is a food, a dietary supplement, a medicine or an OTC (Over The Counter) product.

Preferably, the elder extract according to the present invention is obtained from elder berries and/or flowers, and preferably from elderberries. Advantageously, the elder extract according to the present invention is a water-soluble extract.

The elder extract used within the scope of the present invention can be characterized by its content on the one hand of anthocyans and on the other hand of large molecules such as proteins (in particular lectins).

Preferably, the elder extract contains anthocyans, more preferably belonging to the family of pelargonidins and cyanidins, in an amount between about 0.5% and about 25%, more preferably between about 3% and about 25% and most preferably between about 8% and about 16% by weight, based on the solids content of the extract. Preferably, the anthocyan content is equal to about 12% by weight, based on the solids content of the extract. These contents are expressed as cyanidin-3-glucoside according to the HPLC method described in J. Agric. Food Chem. 2004, 52, 7846-7856.

Preferably, the elder extract contains proteins in an amount between 2 and 10% by weight, preferably between 5% and 10% by weight, and more preferably between 5% and 7% by weight, based on the solids (N×6.25 according to the Kjeldahl method: Protéines végétales, Ed. B. Godon, Collection Sciences et Techniques Agro-alimentaires, Technique et Documentation Lavoisier, Paris, 1985).

Within the scope of the present invention, the elder extract is commercially available or can be obtained by a process comprising the following steps:

Fresh or frozen elderberries can be pressed in order to obtain a juice after filtration. It can be submitted to an enzymatic hydrolysis step (pectinase or a mixture of pectin methylesterase and polygalacturonase) in order to clarify it before filtration (Girard B. and Fukumoto L. R. Membrane processing of fruit juices and beverages: a review. Critical Reviews in Food Science and Nutrition, 2000, 40(2):91-157). The dried and ground berries can also be submitted to aqueous extraction, followed by solid/liquid separation through filtration.

The resulting extracts can be used as such or concentrated, or dried into a powder.

The anthocyan content, at this stage, is between 0.5% and 3% by weight based on the solids content of the extract, and is preferably equal to about 1% (HPLC assay, expressed in cyanidin-3-glucoside).

The elder extract can be supplemented in particular with anthocyans and/or high molecular weight molecules (proteins, polyphenols, polysaccharides). For this purpose, several methods are possible and are well-known to those skilled in the art:

Ultrafiltration: diafiltration step on previously diluted juice followed with overconcentration over an organic or inorganic membrane with a cut-off threshold of between 1 and 20 kDa, and preferably of between 3 and 10 kDa (Girard B. and Fukumoto L. R. Membrane processing of fruit juices and beverages: a review. Critical Reviews in Food Science and Nutrition, 2000, 40(2):91-157).

Passage onto a column of an Amberlite-type absorbent polymeric resin) XAD.

Hydro-alcoholic extraction (a mixture in any proportions of water and C1 to C4 alcohol) or acidic pH aqueous solutions (Bronnum-Hansen K. and Flink J. M. Anthocyanin colorants from elderberry (*Sambucus nigra L.*) IV. Further studies on production of liquid extracts, concentrates and freeze dried powders. Int. J. Food Sci Tech 1986, 21(2):605-614; Lee J. and Wrolstad R. E. Extraction of Anthocyanins and polyphenolics from blueberry processing waste. J. Food Sci. 2004, 69(7):564-573). This extraction can preferably be performed directly on the dried and ground berries or on a puree from fresh berries.

The resulting extract can be thermally concentrated (at a temperature not above 50° C. and under vacuum) in order to increase the Brix degrees and to stabilize it with regard to microbiological contaminations. It can also be dried alone or on a support (for example maltodextrin, lactose . . . ).

The supplemented juice obtained is preferably between 40 and 60° Brix, between 3 and 25% of anthocyans and between 5 and 10% of proteins (Kjeldahl method, N×6.25) by weight based on the solids content.

Preferably, the amount of elder solids per unit dose in the composition, according to the invention, is between about 100 mg and about 1 g. More preferably, the composition contains between about 150 mg and about 500 mg of elder solids per unit dose and more preferably, between about 150 and 300 mg of elder solids per unit dose, most preferably between 200 mg and 250 mg of elder solids per unit dose.

Within the scope of the present invention, the term <<unit dose>> refers to the amount of composition according to the invention administered in one single dosage. Preferably a unit dose according to the present invention can correspond for example to a 100 or 125 ml yoghurt, to a 1 g capsule or to a 2 g tablet. Thus, whatever the weight of the composition, the amount of elder solids and/or *L. paracasei, L. casei, L. bulgaricus* or *S. thermophilus* strain per unit dose remains constant. Preferably, the dosing regimen is two unit doses per day.

One most suitable *L. paracasei* strain within the scope of the present invention is the *L. paracasei* strain deposited on Dec. 30, 1994, at the CNCM (Collection Nationale de Cultures of Microorganisms, 28 rue du Docteur Roux, Paris), under reference number 1-1518. This strain, also known under reference number DN-114 001 or *L. casei* Defensis® (trade name), is the subject of patent EP 0 794 707. The effects of this strain in enhancing a systemic immune response specific to respiratory tract pathogenic micro-organisms (including influenza virus) have been described in patent EP 1 283 714 and its effects on enhancing the protection against influenza after vaccination have been described in patent application FR 2 912 657.

The nomenclature of *Lactobacillus casei* and *paracasei* has been so far the subject of requests for modification and it is still currently disputed. The great majority of strains referred to as *L. casei* or *L. paracasei* subsp. *paracasei* in the literature are currently members of the same species which could be named *Lactobacillus paracasei* subsp. *paracasei* in order to satisfy the current nomenclature.

These bacteria strains can be used in combination with other lactic acid bacteria, or in combination with yoghurt ferments, i.e. *Lactobacillus bulgaricus* and *Streptococcus thermophilus*.

Thus, when *L. paracasei* is used in combination with yoghurt ferments, said composition can further comprise at least $10^7$ and preferably between $5 \times 10^7$ and $2 \times 10^8$ *S. thermophilus* cells per ml, and at least $5 \times 10^4$ and preferably between $10^5$ and $5 \times 10^5$ *L. bulgaricus* cells per ml.

One most suitable *L. bulgaricus* strain within the scope of the present invention is the *L. bulgaricus* strain deposited at the CNCM under reference number I-2787.

One most suitable *S. thermophilus* strain within the scope of the present invention is the *S. thermophilus* strain deposited at the CNCM under reference number I-2130.

The bacteria from these strains can be used in the form of whole, living or non-living bacteria, and also in the form of bacterial lysate, or in the form of bacterial fractions.

These bacteria can also be coated with vegetable fat as described in patent application WO 2005/070221, in order to improve their survival.

Preferably, the composition will contain $1 \times 10^7$ to $1 \times 10^{11}$ CFU of *L. paracasei, L. casei, L. bulgaricus* or *S. thermophilus* per unit dose.

Advantageously, the daily dosage of *L. paracasei, L. casei, L. bulgaricus* or *S. thermophilus* is between $10^8$ and $10^{10}$ CFU.

Preferably, the daily dosing regimen is of two unit doses per day.

In one specific embodiment of the invention, the composition contains, per unit dose,
- 100 mg to 1 g of elder solids, preferably 150 mg to 500 mg, advantageously 150 mg to 300 mg, and more preferably 200 mg to 250 mg; and
- $1 \times 10^7$ to $1 \times 10^{11}$ of *L. paracasei, L. casei, L. bulgaricus* or *S. thermophilus*.

In one specific embodiment of the invention, the composition contains, per unit dose,
- from 3 mg to 200 mg of elder anthocyans, preferably from 10 to 100 mg and more preferably from 20 mg to 50 mg;
- from 2 mg to 100 mg of elder proteins, preferably from 10 mg to 20 mg; and
- $1 \times 10^7$ to $1 \times 10^{11}$ of *L. paracasei, L. casei, L. bulgaricus* or *S. thermophilus*.

Thus advantageously a synergy effect is recorded.

The combination of an elder extract and a strain of *L. paracasei, L. casei, L. bulgaricus* or *S. thermophilus* according to the invention has shown good abilities to induce/stimulate a non-specific immune response thus demonstrating its advantage in the food and/or pharmaceutical fields.

The composition according to the present invention can preferably be found under any galenic forms usually used in the food and/or pharmaceutical fields for oral or sublingual administration.

In the case of a food, this may be in particular fresh dairy products, fermented dairy products, yoghurts, fermented milks, infant milks, powders, lozenges, vegetable juices, beverages, and mixtures thereof, preferably selected from the group consisting of fresh dairy products, fruit and/or vegetable juices, or fruit purees.

Advantageously, the fruit is selected from the group consisting of apple, orange, red berries, strawberry, peach, apricot, plum, raspberry, blackberry, redcurrant, lemon, grapefruit, banana, pineapple, kiwi, pear, cherry, coconut, passion fruit, mango, fig, rhubarb, melon, exotic fruit, litchi, grapes, blueberry, or mixtures thereof.

Preferably, the food according to the invention is a fresh dairy product. Advantageously, it is a fermented dairy product. Most advantageously, it is a fresh fruit-based dairy product.

Preferably with regard to fresh fruit-based dairy products, the elder extract is added to the final product by means of a fruit preparation. The *L. paracasei, L. casei, L. bulgaricus* or *S. thermophilus* strain is in turn mixed into the dairy base as a ferment.

By "fermented dairy product", it should be understood more particularly a fermented dairy product ready for human consumption, that is, a fermented dairy food. In the present application, fermented milks and yoghurts are more particularly provided. Said fermented dairy foods can alternatively be "fromage blanc" or "petit-suisse".

As used herein, the terms "fermented milks" and "yoghurts" have their usual meanings in the field of dairy industry, i.e. products intended for human consumption, and resulting from acidifying lactic fermentation of a dairy substrate. These products can contain secondary ingredients such as fruit, plants, sugar, etc. For example refer to French Order No. 88-1203 of Dec. 30, 1988 relating to fermented milks and yogurt or yoghurt, published in the Journal Officiel de la République Française on Dec. 31, 1988. Also refer to "Codex Alimentarius" (prepared by the Commission of the Codex Alimentarius under the auspices of the FAO and the WHO, and published by the Information Division of the FAO, available on-line at http://www.codexalimentarius.net; cf. more particularly Volume 12 of the Codex Alimentarius "Codex Standards for milk and dairy products", and the standard "CODEX STAN A-1 1(a)-1975").

In the present application the term "fermented milk" is thus only used to designate a dairy product prepared with a dairy substrate which has been submitted to a process at least equivalent to pasteurization, seeded with microorganisms belonging to the species characteristic of each product. A "fermented milk" has not been subjected to any process subtracting a constituent element of the dairy substrate employed, and in particular has not been subjected to a draining of the coagulum. The coagulation of "fermented milks" should not be obtained by other means than those resulting from the activity of the microorganisms used. In practice, the term "fermented milk" is thus generally used to designate fermented milks other than yoghurts, and can be referred to, according to the country, as "Kefir", "Kumiss", "Lassi", "Dahi", "Leben", "Filmjolk", "Villi", "Acidophilus milk", for example.

As for the term "yoghurt", it is used to designate fermented milk obtained traditionally and consistently by the development of thermophilic lactic acid bacteria specific to said *Lactobacillus bulgaricus* and *Streptococcus thermophilus*, which should be left alive in the finished product, in an amount of at least 10 million bacteria per gram based on the milk part. In some countries, the regulations authorize the addition of other lactic acid bacteria in the production of yoghurt, and in particular the additional use of *Bifidobacterium* and/or *Lactobacillus acidophilus* strains. These additional lactic strains aim at conferring to the finished product various properties, such as the property of promoting the intestine flora balance, or to control the immune system.

The amount of free lactic acid contained in the fermented dairy substrate should not be lower than 0.6 g per 100 g when sold to the consumer, and the protein matter content provided to the milky part should not be lower than that of regular milk.

The name "fromage blanc" or "petit-suisse" in the present application is used to designate exclusively a non ripened, non salted, cheese that has been fermented with lactic acid bacteria only (no other fermentation than lactic acid fermentation). The solids content in fromage blanc can be reduced down to 15 g or 10 g per 100 g of fromage blanc, according to whether its fat content is 25% higher than 20 g, or at most equal to 20 g, per 100 g of fromage blanc, when completely dried. The solids content of a fromage blanc is between 13 and 20%. As for the solids content of a petit-suisse, it is not lower than 23 g per 100 g of petit-suisse. It is generally between 25 and 30%. Fromage blanc and petit-suisse are generally commonly referred to as <<cottage cheese>> traditionally used in the technical field of the present invention.

Preferably, the fresh dairy product is selected from yoghurts including stirred yoghurts, drinking yoghurts, cottage cheese and fermented milks.

Within the meaning of the present invention, <<dietary supplement>> refers to a food product intended to complement a normal diet and which is a concentrated source of nutriments or other substances having a dietary or physiologic effect alone or in combination.

Preferably, the dietary supplement can comprise vitamins and/or minerals and/or trace elements.

These vitamins include in particular the vitamins A, E, C, and the B group vitamins, in particular vitamin B6. Advantageously, these are vitamins C, E and B6.

Vitamin A (retinol or carotenoids), vitamin E and vitamin C are the 3 major anti-oxidizing vitamins. In fact, these antioxidizing vitamins have the ability of controlling the production of free radicals resulting from oxygen metabolism, the overproduction of which is responsible for a large number of conditions, especially cardio-vascular, immunity, cancer, skin, accelerated ageing, neurodegenerative diseases, etc.

In particular, vitamin C is a well known antioxidizing agent, which is soluble in water. Human beings rely on external sources of vitamin C to meet their vitamin C requirements. Thus, ascorbic acid, sodium ascorbate, or a mixture thereof, are a source of vitamin C.

Vitamin E is also a well known antioxidizing agent. Vitamin E can function synergistic with vitamin C in order to protect the vital cell function against normal oxidizing agents. Alpha-tocopheryl acetate, trimethyl-tocopheryl acetate and/or vitamin E succinate are sources of vitamin E.

Vitamins B form a group of water-soluble vitamins that include vitamin B1 or thiamine, vitamin B2 or riboflavin, vitamin B3 (PP) or nicotinamide, vitamin B5 or pantothenic acid, vitamin B6 or pyridoxine, vitamin B8 (H) or biotin, vitamin B9 or folic acid, vitamin B12 or cyanocobalamine.

Preferably, the minerals are selected from iron, zinc, selenium, chromium, copper and mixtures thereof.

Zinc has an antioxidizing action as a cofactor for those enzymes which are directly involved in the defense against oxidizing agents. Zinc oxide, zinc gluconate, zinc citrate, zinc acetate, zinc chloride, zinc lactate or zinc sulfate can be used alone or as a mixture in the compositions according to the present invention. Zinc gluconate is preferred.

Selenium has also an antioxidizing action as a cofactor (such as glutathione peroxidase) for those enzymes which are directly involved in the defense against oxidizing agents.

In the case of a dietary supplement or a medicine, the following galenic forms can be envisaged: swallowable tablets, chewable tablets, effervescent tablets, capsules, lozenges, pills, powders, granules, oral solutions or suspensions and sublingual and buccal dosage forms. Preferred galenic forms are tablets or capsules.

When a solid composition is prepared in the form of tablets, the main active ingredient can be mixed with a pharmaceutical carrier such as gelatin, starch, lactose, magnesium stearate, talcum, gum Arabic, or the like. The tablets can be coated with sucrose or other suitable materials, or can be processed so as to have a sustained or delayed action and to continuously release a predetermined amount of active principle.

A capsule preparation is prepared by mixing the active ingredient with a diluent and by filling the resulting mixture into soft or hard capsules.

A preparation in the form of syrup or elixir can contain the active ingredient together with a sweetener, an antiseptic, as well as a flavoring agent and a suitable colorant.

The water-dispersible powders or granules can contain the active ingredient as a mixture with dispersing agents or wetting agents, or suspending agents, as well as with taste correctors or sweeteners.

Another object of the present invention is a composition according to the present invention for use as a medicine.

Another object of the present invention is a composition according to the present invention for stimulating immunity and/or enhancing immune defenses, and/or promoting an anti-infectious and/or anti-inflammatory response.

Another object of the present invention is a composition for use in the treatment and/or prevention of respiratory and/or intestinal infections.

Another object of the present invention is a composition for use in the treatment and/or prevention of symptoms caused in particular by an infection by type 1 herpes simplex virus, respiratory syncytial virus, and Influenza (A and/or B and/or C) and parainfluenza virus, preferably the symptoms of influenza conditions, especially caused by the Influenza (A and/or B and/or C) virus.

The composition according to the invention is particularly suitable for the treatment and/or prevention of symptoms of influenza conditions caused by an infection by Influenza viruses (*Orthomyxovirus, Influenzae* A, B or C). These symptoms include colds, rhinitis, cough, inflammations of the nasal mucous membrane (rhinorrhea, nasal obstruction, sneezing events), sore throat (various expressions: tingles, swallowing difficulties), fever, headache, muscle soreness, fatigue.

These <<winter troubles>> are associated with the weakening of our immune defenses.

Another object of the present invention is the use of the composition for preparing a food, a dietary supplement or a medicine.

Another object of the present invention is the use of the composition for preparing a medicine intended for the treatment and/or prevention of respiratory and/or intestinal infections.

Another object of the present invention is the use of the composition for preparing a medicine intended for the treatment and/or prevention of symptoms of an infection by the type 1 herpes simplex virus, the respiratory syncytial virus and the Influenza (A and/or B and/or C) and parainfluenza virus, preferably symptoms of influenza conditions, especially caused by the Influenza (A and/or B and/or C) virus.

Another object of the present invention is the use of the composition for preparing a medicine for use in stimulating immunity and/or promoting an anti-infectious and/or anti-inflammatory response.

Yet another object of the present invention is to provide a process for enhancing immune defenses comprising oral administration of a composition based on a combination of an elder extract and at least one strain of *L. paracasei, L. casei, L. bulgaricus* or *S. thermophilus*.

The description refers to the attached figures in which.

| Legend of FIG. 1 | |
|---|---|
| ● | Elder extract |
| ○ | (elder + *L. paracasei* CNCM I-1518) theoretical |
| ◈ | (elder + *L. paracasei* CNCM I-1518) experimental |

| Legend of FIG. 2 | |
|---|---|
| ● | *L. paracasei* CNCM I-1518 |
| ○ | (*L. paracasei* CNCM I-1518 + elder) theoretical |
| ◈ | (*L. paracasei* CNCM I-1518 + elder) experimental |

| Legend of FIG. 3 | |
|---|---|
| ● | *L. paracasei* CNCM I-1518 |
| ○ | (*L. paracasei* CNCM I-1518 + elder) theoretical |
| ◈ | (*L. paracasei* CNCM I-1518 + elder) experimental |

| Legend of FIG. 4 | |
|---|---|
| ● | *L. casei* |
| ○ | (*L. casei* + elder) theoretical |
| ◈ | (*L. casei* + elder) experimental |

| Legend of FIG. 5 | |
|---|---|
| ● | *L. bulgaricus* CNCM I-2787 |
| ○ | (*L. bulgaricus* CNCM I-2787 + elder) theoretical |
| ◈ | (*L. bulgaricus* CNCM I-2787 + elder) experimental |

| Legend of FIG. 6 | |
|---|---|
| ● | *S. thermophilus* CNCM I-2130 |
| ○ | (*S. thermophilus* CNCM I-2130 + elder) theoretical |
| ◈ | (*S. thermophilus* CNCM I-2130 + elder) experimental |

| Legend of FIG. 7 | |
|---|---|
| ● | *L. brevis* |
| ○ | (*L. brevis* + elder) theoretical |
| ◈ | (*L. brevis* + elder) experimental |

| Legend of FIG. 8 | |
|---|---|
| ▓ | complete formulation |
| ▲ | vitamins + minerals |
| ◈ | elderberry extract |
| ⋯ | vehicle |
| ● | *L. paracasei* + dairy mix |

The invention will be better understood by reference to the following non limiting examples which are specific embodiments of the compositions according to the invention.

EXAMPLE 1

Preparation of an Elder Extract used within the Scope of the Present Invention

The elder extract is obtained from elderberry juice enriched with anthocyans and dried over maltodextrin. The enrichment was carried out using a membrane filtration process according to the method below:

26 liters of clarified elder juice are diluted with 284 liters of water (11 volumes of water per 1 volume of juice). The resulting 310 liters are stirred and heated to 45° C. then diafiltrated on a first 5 kDa membrane with addition of 7 volumes of water by volume of juice (i.e. 181 L). The dialysis permeate is then concentrated by ultrafiltration on a 5 kDa membrane (5/10 kDa pilot membrane having a unit surface area of 5.8 m²). The ultrafiltration retentate is thermally concentrated under vacuum at a temperature not above 50° C., then atomized onto a maltodextrin support so that the amount of maltodextrin is lower than or equal to 30% (w/w). The characteristics of the resulting extract are:

Anthocyan content: 10-14% by weight based on the solids content of the extract (expressed as cyanidine-3-glucoside according to the HPLC method described in *J Agric Food Chem* 2004, 52, 7846-7856)

Protein content: 5-7% by weight based on the solids content of the extract (N×6.25 according to the Kjeldahl method)

EXAMPLE 2

In Vitro Study of Combined Immunomodulator Effects of the *L. paracasei* Strain CNCM 1-1518 with an Elder Extract in Peripheral Blood Mononuclear Cells (PBMC)

Material and Method

Peripheral blood mononuclear cells (PBMC) are isolated from healthy subjects, resuspended and distributed in 24-well plates at $0.5 \times 10^6$ cells/well. These PBMC are incubated overnight at 37° C. with either various concentrations of elder extract (3-10-30-100 µg/ml of PBMC cell culture supernatant) in the presence or in the absence of an amount of *L. paracasei* (4.5 *L. paracasei* per 1 PBMC), or alternatively with different *L. paracasei*:PBMC ratios (0.5:1-1:1-2:1-4.5:1) in the presence or in the absence of elder extract at 10 µg/ml of PBMC cell culture supernatant.

The elder extract used was prepared according to Example 1.

The culture supernatants are recovered for determining the cytokins (IL-10 and IFN-gamma) by flux cytometry.

Within the scope of the present combination, the combined elder and *L. paracasei* do not have the same measurement unit, i.e. a concentration in µg/ml and a ratio of number of bacteria:PBMC, respectively.

In order to determine whether the elder extract+*L. paracasei* combination produces a synergy effect, the inventors used the method described in the publication of Etievant C, Kruczynski A, Barret J M and al. <<F 11782, a dual inhibitor of topoisomerases I and II with an original mechanism of action in vitro, and markedly superior in vivo antitumour activity, relative to three other dual topoisomerase inhibitors, intoplicin, aclarubicin and TAS-103>> Cancer Chemother. Pharmacol. 2000; 46: 101-113.

This publication teaches the comparison and interpretation of the experimental results, compared with the plotting of a theoretical curve.

The latter is based on variable experimental data for one compound (e.g. an increasing elder extract concentration) and on a fixed experimental data for the second compound (e.g. a fixed ratio of number of bacteria:PBMC).

Figure 1:
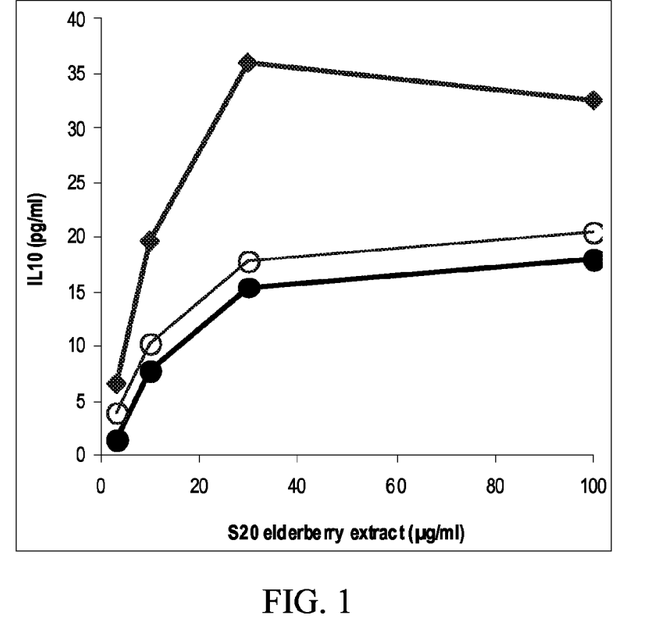
FIG. 1 shows the production of IL-10 induced by an elder extract alone or in combination with a *L. paracasei*:PBMC ratio of 4.5:1.

The theoretical curve in FIG. 1, which shows the production of IL-10 induced by a range of elder extract doses in combination with a fixed *L. paracasei*:PBMC ratio of 4.5:1, was plotted by adding to each experimental point of the curve for the elder alone (●) the contribution of the *L. paracasei*:PBMC ratio of 4.5:1. This contribution, as determined experimentally, is 2.4 pg/ml of IL-10.

Table of the data in FIG. 1

|  |  | Elder concentration (µg/ml) | | | |
|---|---|---|---|---|---|
|  |  | 3 | 10 | 30 | 100 |
| IL-10 (pg/ml) | Elder extract (●) | 1.5 | 7.8 | 15.4 | 18 |
|  | (elder + *L. paracasei*) theoretical (○) | 3.9 (1.5 + 2.4) | 10.2 (7.8 + 2.4) | 17.8 (15.4 + 2.4) | 20.4 (18 + 2.4) |
|  | (elder + *L. paracasei*) experimental (◆) | 6.6 | 19.7 | 36 | 32.5 |

Figure 2:
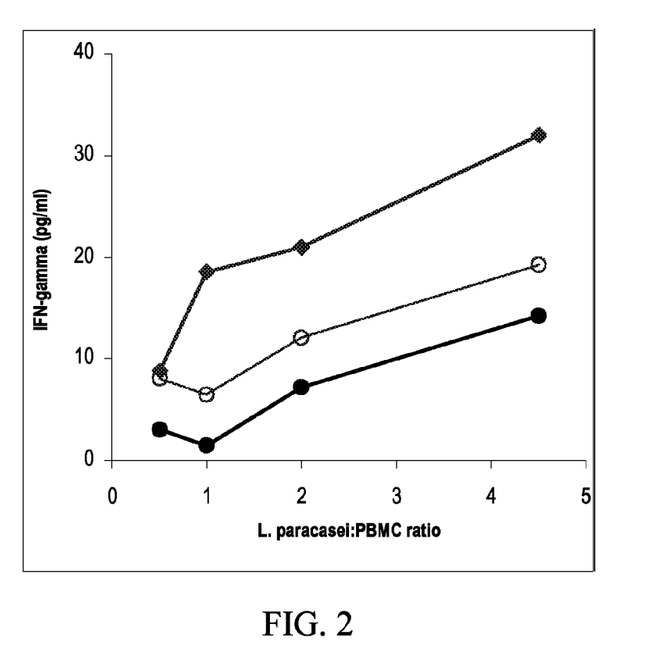
FIG. 2 shows the production of IFN-gamma induced by *L. paracasei* alone or in combination with an elder extract at 10 μg/ml.

The theoretical curve in FIG. 2, which shows the production of IFN-gamma induced by a range of *L. paracasei* doses in combination with an elder extract at the fixed concentration of 10 µg/ml, was plotted by adding to each experimental point of the curve for *L. paracasei* alone (●) the contribution of the elder extract at 10 µg/ml. This contribution, determined experimentally, is 5 pg/ml of IFN-gamma.

Table of the data for FIG. 2

|  |  | *L. paracasei*:PBMC ratio | | | |
|---|---|---|---|---|---|
|  |  | 0.5:1 | 1:1 | 2:1 | 4.5:1 |
| IFN-γ (pg/ml) | *L. paracasei* (●) | 3 | 1.5 | 7.1 | 14.2 |
|  | (*L. paracasei* + elder) theoretical (○) | 8 (3 + 5) | 6.5 (1.5 + 5) | 12.1 (7.1 + 5) | 19.2 (14.2 + 5) |
|  | (*L. paracasei* + elder) experimental (◆) | 8.7 | 18.5 | 20.9 | 31.9 |

Results

FIGS. 1 and 2 give the results obtained:
  FIG. 1 shows the production of IL-10 induced by an elder extract alone or in combination with a *L. paracasei*:PBMC ratio of 4.5:1
  FIG. 2 represents the production of IFN-gamma induced by *L. paracasei* alone or in combination with an elder extract at 10 µg/ml.

The effect on the non-specific immune response induced by the elder extract alone or in combination with a particular *L. paracasei*:PBMC ratio (4.5:1) was studied.

The cytokine concentration obtained with a *L. paracasei*:PBMC ratio of 4.5:1 is 2.4 pg/ml.

A comparison of the results obtained experimentally with the values of the theoretical curve show that *L. paracasei* potentiates the effect of the elder extract alone: the combination provides an IL-10 production that is much higher than the sum of the 2 effects (elder extract on the one hand and *L. paracasei* on the other hand).

The inventors also examined the effect of various *L. paracasei*:PBMC ratios, alone or in combination with a fixed elder extract concentration (10 µg/ml) on the gamma-interferon production.

The cytokine concentration obtained with the elder extract at the concentration of 10 µg/ml is 5 pg/ml.

A comparison of the various curves obtained show that the elder extract potentiates the effect of *L. paracasei*: the combination provides an IFN-gamma production that is higher than the sum of the 2 effects (*L. paracasei* on the one hand and elder extract on the other hand).

Conclusion:

The elder extract and *L. paracasei* CNCM 1-1518 (DN-114 001) act synergistic on non-specific immune responses, thus making the human immune system cells more reactive against infectious aggressions or morbid inflammatory processes.

EXAMPLE 3

In Vitro Study of the Strain Specificity

Material and Method

Peripheral blood mononuclear cells (PBMC) are isolated from healthy subjects, resuspended and distributed in 24-well plates at $0.5 \times 10^6$ cells/well. These PBMC are incubated overnight at 37° C. with different strain:PBMC ratios (0.5:1-1:1-2:1-4.5:1) in the presence or in the absence of elder extract at 10 µg/ml of PBMC cell culture supernatant.

The elder extract used was prepared according to Example 1.

Five strains have been tested for this in vitro study: a *Lactobacillus paracasei* (CNCM 1-1518) strain, a *Lactobacillus casei* strain, a *Lactobacillus bulgaricus* (CNCM 1-2787) strain, a *Streptococcus thermophilus* (CNCM 1-2130) strain and a *Lactobacillus Brevis* strain.

The culture supernatants are recovered for determining the cytokine IL-6 by ELISA.

In order to determine whether the elder extract/strain combinations produce a synergy effect, the method described in the publication of Etievant C. et al (see above) was used. This publication teaches the comparison and interpretation of the experimental results, compared with the plotting of a theoretical curve.

The latter is based on variable experimental data for the increasing number of bacteria:PBMC ratio and on a fixed experimental data for the elder extract concentration.

The theoretical curves in FIG. 3-7, which show the production of IL-6 induced by a range of strain doses in combination with an elder extract at the fixed concentration of 10 µg/ml, were plotted by adding to each experimental point of the curve for strain alone ( ● ) the contribution of the elder extract at 10 µg/ml. This contribution was determined experimentally for each experiment.

Results

Figure 3:
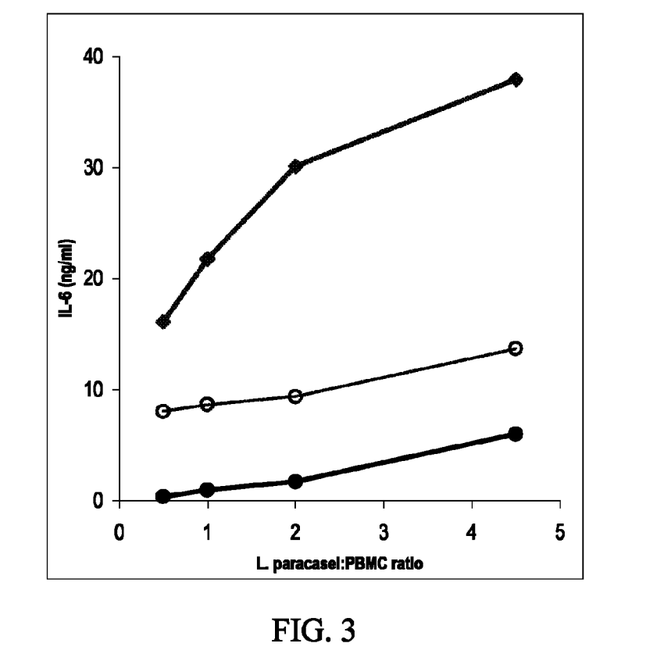
FIG. 3 shows the production of IL-6 induced by *L. paracasei* alone or in combination with an elder extract at 10 μg/ml.
Figure 4:
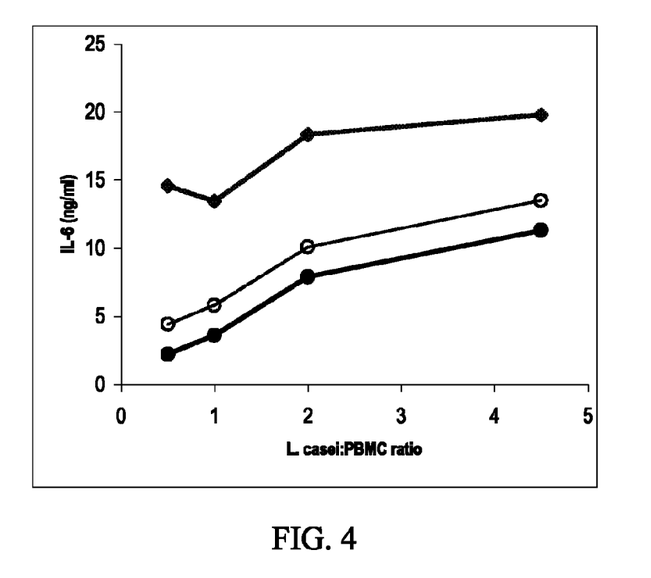
FIG. 4 shows the production of IL-6 induced by a *L. casei* strain alone or in combination with an elder extract at 10 μg/ml.
Figure 5:
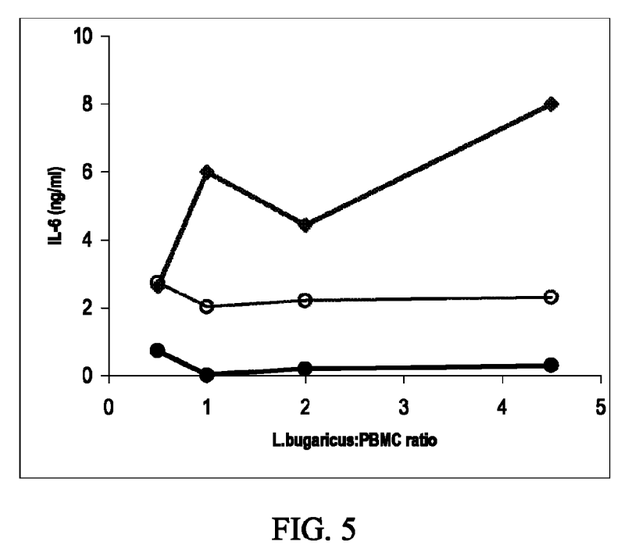
FIG. 5 shows the production of IL-6 induced by *L. bulgaricus* alone or in combination with an elder extract at 10 μg/ml.
Figure 6:
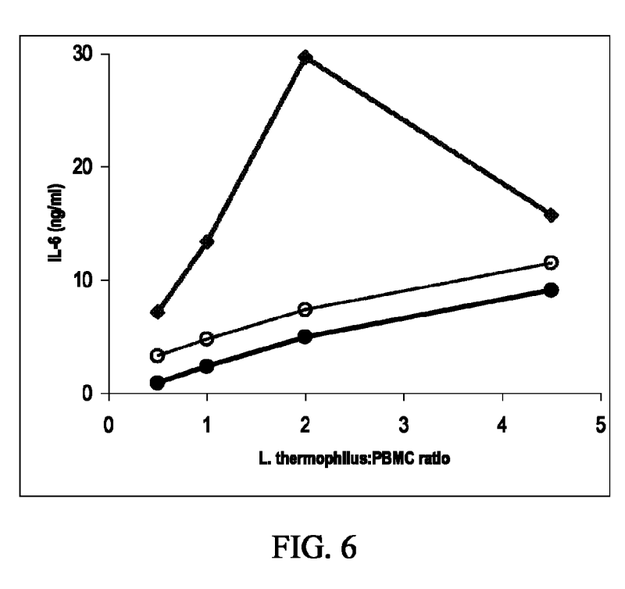
FIG. 6 shows the production of IL-6 induced by *S. thermophilus* alone or in combination with an elder extract at 10 μg/ml.
Figure 7:
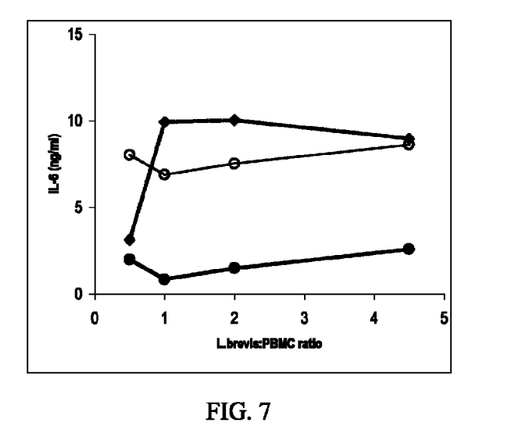
FIG. 7 shows the production of IL-6 induced by a *L. brevis* strain alone or in combination with an elder extract at 10 μg/ml.

FIGS. 3 to 7 give the results obtained:

FIG. 3 represents the production of IL-6 induced by *L. paracasei* alone or in combination with an elder extract at 10 µg/ml (the cytokine concentration obtained with the elder extract at the concentration of 1 µg/ml is 7.7 ng/ml);

FIG. 4 represents the production of IL-6 induced by *L. casei* alone or in combination with an elder extract at 10 µg/ml (the cytokine concentration obtained with the elder extract at the concentration of 1 µg/ml is 2.2 ng/ml);

FIG. 5 represents the production of IL-6 induced by *L. bulgaricus* alone or in combination with an elder extract at 10 µg/ml (the cytokine concentration obtained with the elder extract at the concentration of 10 µg/ml is 2.0 ng/ml);

FIG. 6 represents the production of IL-6 induced by *S. thermophilus* alone or in combination with an elder extract at 10 µg/ml (the cytokine concentration obtained with the elder extract at the concentration of 10 µg/ml is 2.4 ng/ml);

FIG. 7 represents the production of IL-6 induced by *L. brevis* alone or in combination with an elder extract at 10 µg/ml (the cytokine concentration obtained with the elder extract at the concentration of 1 µg/ml is 6.0 ng/ml).

The effect of various strain:PBMC ratios, alone or in combination with a fixed elder extract concentration (10 µg/ml) on IL-6 production was studied for 5 different strains.

The experiment carried out with *L. paracasei* (FIG. 3) confirms that the elder extract potentiates the effect of *L. paracasei*: the combination provides an IL-6 production that is higher than the sum of the 2 effects (*L. paracasei* on the one hand and elder extract on the other hand).

This type of synergy has been observed too with *L. casei, L. bulgaricus*, or *S. thermophilus* but not with *L. brevis* showing that the synergistic effect is strain specific.

Conclusion:

It has been confirmed that the elder extract and *L. paracasei* act synergistic on non-specific immune responses, thus making the human immune system cells more reactive against infectious aggressions or morbid inflammatory processes.

Furthermore it has been observed that the synergistic effect is strain specific. The elder extract and *L. casei, L. bulgaricus*, or *S. thermophilus* act synergistic on non-specific immune responses.

On the contrary no synergy was observed for the elder extract and *L. brevis* association. Thus, this strain could serve as negative control for other investigations.

EXAMPLE 4

In Vivo Study of the Cytotoxic Activity of Splenocytes from Mice Receiving a Complete Formulation Introduction As demonstrated in examples 2 and 3, elderberry extract and probiotics such as *L. paracasei* DN-114 001 in vitro synergizes in order to produce increased cytokine production. The aim of this study was to evaluate the effect of the complete formulation in vivo on an immune function and to compare its activity to each group of ingredients:

*L. paracasei*+dairy mix
elderberry extract
mix of vitamins and mineral salts=Vitamins+minerals The elder extract used was prepared according to Example 1.

The complete formulation is a combination of the following ingredients: *L. paracasei*+dairy mix, the elderberry extract, the mix of vitamins and mineral salts and the excipients. The amount administered for each ingredient of the 3 groups of ingredients is equal to the corresponding amount of the ingredient present in the complete formulation.

For this purpose, the inventors choose to monitor the natural killer (NK) cell function. Indeed, the innate immune responses, including NK cells, are critical for host defence against respiratory viruses. NK cells represent a distinct lymphocyte subpopulation that plays an important role in the early phase of immune responses against certain viruses, parasites, and microbial pathogens (3) by exhibiting cytotoxic functions. Moreover, there is increasing evidences that NK cells have important functions in influencing the nature of the adaptive immune response (1; 2).

Materials and Methods

Animals and Treatments

BALB/c female mice, 7 weeks old, were randomly assigned to one of five groups:

Group 1→Vehicle (sterile water)
Group 2→Complete Formulation (1500 mg/kg)
Group 3→*L. paracasei* DN-114 001+dairy mix (393 mg/kg)
Group 4→Elderberry extract (296 mg/kg)
Group 5→Vitamins+Minerals (282 mg/kg)

They were orally treated on D0, D1 and D2, with 10 ml/kg of test product. On D9, mice were sacrificed and spleen were removed.

Cytotoxicity Assay

Cytolytic activity against targets was determined using the CytoTox 96 nonradioactive cytotoxicity assay. Splenocytes were collected from mice and co-cultured with YAC-1 cells (mouse T lymphoma cell line) as target cells at appropriate effector-to-target cell count ratios in 96 V-bottomed plates. After 4 hours of incubation at 37° C., the amount of released lactate dehydrogenase (LDH) was measured in supernatants. The amount of LDH released was measured using LDH substrate and evaluated at 490 nm. For each mouse, the average percent NK cytotoxicity (%) at three effector/target ratios (100:1-50:1- and 25:1) was determined using the following formula:

$$[A_{490} \text{ experimental release} - (A_{490} \text{ Effector cell spontaneous release} + A_{490} \text{ Target cell spontaneous release}) \times 100]/(A_{490} \text{ Target cell maximal release} - A_{490} \text{ Target cell spontaneous release}).$$

Statistical Analysis

Statistical analysis was performed using the SigmaStat 3.5 package for Windows. Results were evaluated with the One Way Analysis of Variance followed by a multiple comparison group using the Holm-Sidak method. P<0.05 was considered statistically significant in all cases.

Results

Figure 8:
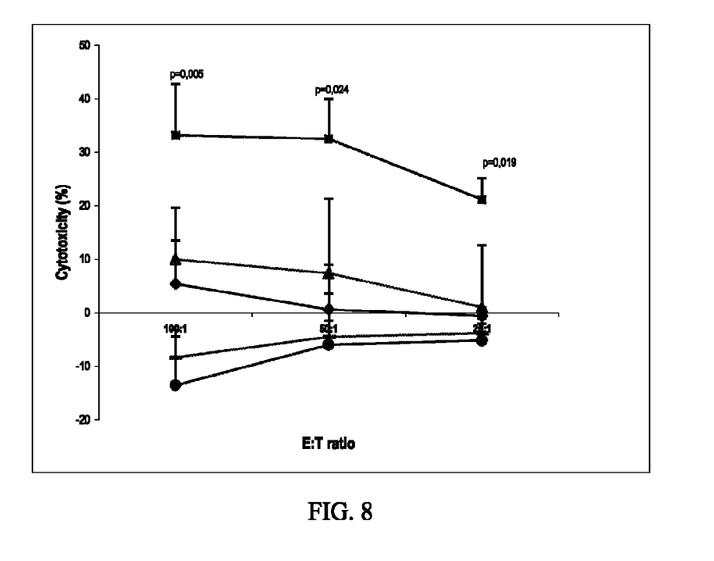
FIG. 8 represents the NK cell cytotoxic activity from mice receiving the vehicle (green), the complete formulation (1500 mg/kg; red), *L paracasei* DN-114 001+dairy mix (393 mg/kg; blue), the elderberry extract (296 mg/kg; violet) or vitamins+minerals (282 mg/kg; grey). P values: complete formulation as compared to vehicle.

The cytotoxic activity of splenocytes from mice receiving the complete formulation or each ingredient was investigated. Splenocytes from mice immunised with the complete formulation exerted significantly increased cytotoxic activities against YAC-1 target cells compared with those from mice receiving the vehicle (water) (FIG. 8). In contrast, mice immunised with individual ingredients failed to increased cytotoxic activities against YAC-1 target cells.

Conclusion

These data clearly show that the combination of ingredients individually inefficient on the activation of NK cells, become fully active when combined in appropriate amounts.

REFERENCES

1. Di Santo, J. P. Natural killer cell developmental pathways: a question of balance. *Annu. Rev. Immunol.* 24, 257-286 (2006)
2. Vivier, E., Tomasello, E., Baratin, M., Walzer, T. & Ugolini, S. Functions of natural killer cells. *Nat. Immunol.* 9, 503-510 (2008)
3. Lodoen, M. B. & Lanier, L. L. Natural killer cells as an initial defense against pathogens. *Curr. Opin. Immunol.* 18, 391-398 (2006).

EXAMPLE 5

Dietary Supplement

Any type of dietary supplement could be considered. As an example, the unit dose could be a 1 g capsule or to a 2 g tablet. The general composition is as follows:

| | |
|---|---|
| Elder solids (according to Example 1) | 30% |
| Fermented milk powder containing *L. paracasei* DN-114 001 | 40% |
| Vitamin mix (vitamins C, E and B6) | 24-27% |
| Zinc gluconate (Zinc) | 2-5% |
| Sodium selenate (Selenium) | 0.1-0.5% |

Therefore the *L. paracasei* DN-114 001 population of the tablet or capsule is $2\times10^{10}$ CFU at the end of the preparation process.

This dietary supplement is made by methods well known to those skilled in the art. In particular the *L. paracasei* strain and the elder extract are added independently of one another to the composition for obtaining as examples the tablet or capsule.

EXAMPLE 6

Fermented Dairy Product

The unit dose corresponds to 100 ml of fermented dairy product. However it should be noted that, for example, 100 g of Actimel® corresponds to 94-97 ml of product depending on the light or standard recipe considered.

The fermented dairy product contains (in % by weight):
95% of dairy product fermented by a *L. paracasei* DN-114 001 strain (CNCM I-1518) (Actimel® type product) and by commercial strains of *Lactobacillus bulgaricus* and *Streptococcus thermophilus*.

5% of a traditional red fruit preparation containing 5% of concentrated elder extract juice such as described in Example 1.

The solids content of the fermented dairy product is about 17% before drying.

Composition of the fermented dairy product (standard ingredients in % by weight):
77% standard skimmed milk (3.64% milk proteins)
9.6% pasteurized cream
5.7% concentrated skimmed milk
0.6% skimmed milk proteins
6.6% sucrose
0.5% dextrose (Cargill)
DN-114 001 (CNCM 1-1518) Ferment: $10^8$-$10^9$ CFU/ml
Ferment consisting of several commercial strains of *L. bulgaricus* and *S. thermophilus* at populations globally of $10^7$ CFU/ml to $10^8$ CFU/ml.

The traditional fruit preparations, supplemented with elder extract concentrated juice, is added after heat treatment to the fermented dairy product.

Characteristics of the Finished Product:
250 mg of elder solids per 100 g of this product i.e. for a unit dose, that is, 1.47% by weight of elder solids based on the solids weight of the unit dose.

Anthocyan content: 25 mg/100 g i.e. for a unit dose, that is, 0.147% by weight of anthocyans based on the solids weight of the unit dose.

*L. paracasei* Population: $10^8$ cfu/ml for a 100 ml fermented product.

The invention claimed is:

1. A method for stimulating immunity and/or enhancing immune defenses and/or promoting an anti-infectious and/or anti-inflammatory response, comprising:
   administering an effective amount of a composition comprising a combination of an elder extract and at least one strain of *Lactobacillus paracasei, Lactobacillus bulgaricus* or *Streptococcus thermophilus*,
   wherein said at least one strain of *Lactobacillus paracasei* is the strain *Lactobacillus paracasei* deposited at the Collection Nationale de Cultures of Microorganisms (CNCM) under number I-1518, said at least one strain of *Lactobacillus bulgaricus* is the strain *Lactobacillus bulgaricus* deposited at the CNCM under number I-2787, and said at least one strain of *Streptococcus thermophilus* is the strain *Streptococcus thermophilus* deposited at the CNCM under number I-2130, and
   wherein said composition does not comprise a mixture of *Uncaria Tomentosa*, Pau d'Arco, *Scutellaria baicalensis* and artemisinine,
   to a patient in need thereof.

2. The method of claim 1, wherein the composition comprises a combination of an elder extract and at least one strain of *Lactobacillus paracasei*.

3. The method of claim 1, wherein the elder extract comprises anthocyan between 0.5 and 25% by weight based on the solids content of the extract, and protein between 2 and 10% by weight based on the solids content of the extract.

4. The method of claim 1, wherein the composition comprises an amount of *L. paracasei, L. bulgaricus* or *S. thermophilus* of between $1\times10^7$ to $1\times10^{11}$ CFU/unit dose.

5. The method of claim 1, wherein the composition is a food selected from the group of foods consisting of: dairy products, fermented dairy products, yoghurts, fermented milks, infant milks, powders, lozenges, vegetable juices, beverages and mixtures thereof.

6. The method of claim 1, wherein the composition is a dietary supplement or a medicine in a galenic form selected from the group consisting of: swallowable tablets, chewable tablets, effervescent tablets, capsules, lozenges, pills, powder, granules, oral solutions or suspensions, and sublingual and buccal dosage forms.

7. The method of claim 1, wherein the composition contains between 150 mg and 300 mg elder solids per unit dose, and between $1\times10^7$ and $1\times10^{11}$ CFU of *L. paracasei, L. bulgaricus* or *S. thermophilus* per unit dose.

8. The method of claim 5, wherein the composition is a food selected from the group of foods consisting of: fresh dairy products, fruit and/or vegetable juices, and fruit purees.

* * * * *